US009770302B2

(12) United States Patent
Kang et al.

(10) Patent No.: US 9,770,302 B2
(45) Date of Patent: Sep. 26, 2017

(54) METHODS AND SYSTEMS FOR PLANNING AND PERFORMING AN OSTEOTOMY

(71) Applicant: MAKO Surgical Corp., Ft. Lauderdale, FL (US)

(72) Inventors: Hyosig Kang, Weston, FL (US); Snehal Kasodekar, Plantation, FL (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 350 days.

(21) Appl. No.: 13/725,706

(22) Filed: Dec. 21, 2012

(65) Prior Publication Data
US 2014/0180341 A1   Jun. 26, 2014

(51) Int. Cl.
*A61B 17/80* (2006.01)
*A61B 19/00* (2006.01)
*A61B 17/16* (2006.01)
*A61B 34/00* (2016.01)
*A61B 34/10* (2016.01)
*A61B 17/15* (2006.01)
(Continued)

(52) U.S. Cl.
CPC .............. *A61B 19/50* (2013.01); *A61B 17/16* (2013.01); *A61B 17/8095* (2013.01); *A61B 34/10* (2016.02); *A61B 34/70* (2016.02); *A61B 17/151* (2013.01); *A61B 2034/105* (2016.02); *A61B 2034/108* (2016.02); *A61B 2034/2055* (2016.02); *A61B 2090/3983* (2016.02)

(58) Field of Classification Search
None
See application file for complete search history.

(56) References Cited

U.S. PATENT DOCUMENTS

D616,908 S   6/2010   Labak
7,747,311 B2   6/2010   Quaid, III
(Continued)

FOREIGN PATENT DOCUMENTS

CN   101155559 A   4/2008
CN   101448468 A   6/2009
(Continued)

OTHER PUBLICATIONS

U.S. Appl. No. 13/562,163, filed Jul. 30, 2012, Kang, et al.
International Search Report and Written Opinion for PCT Application No. PCT/US2013/076663, dated Apr. 8, 2014, 14 pages.

*Primary Examiner* — Samuel Hanna
(74) *Attorney, Agent, or Firm* — Foley & Lardner LLP

(57) ABSTRACT

A method for performing an open wedge osteotomy includes providing a fixation plate defining a first aperture and a second aperture and creating a first hole and a second hole in a bone. The fixation plate is coupled to the bone by aligning the first aperture of the fixation plate and the first hole of the bone and inserting a fastener through the first aperture and into the first hole. A cut is created through at least a portion of the bone to create a first resected surface and a second resected surface after creating the first hole and the second hole. The method further includes moving the first resected surface and the second resected surface relative to each other until the second aperture of the fixation plate is aligned with the second hole of the bone. The fixation plate is coupled to the bone by inserting a second fastener through the second aperture of the fixation plate and into the second hole of the bone.

5 Claims, 8 Drawing Sheets

(51) Int. Cl.
 A61B 90/00 (2016.01)
 A61B 34/20 (2016.01)

(56) References Cited

U.S. PATENT DOCUMENTS

| | | |
|---|---|---|
| D622,854 S | 8/2010 | Otto et al. |
| 7,799,084 B2 | 9/2010 | Clemow et al. |
| 8,206,053 B2 | 6/2012 | Bennett et al. |
| 8,249,345 B2 | 8/2012 | Wu et al. |
| 8,287,522 B2 | 10/2012 | Moses et al. |
| 2006/0190086 A1 | 8/2006 | Clemow et al. |
| 2007/0219561 A1* | 9/2007 | Lavallee ............ A61B 17/025 606/90 |
| 2008/0010706 A1* | 1/2008 | Moses ................ A61B 19/5244 600/407 |
| 2008/0262812 A1 | 10/2008 | Arata et al. |
| 2009/0054762 A1 | 2/2009 | Burgkart |
| 2009/0306499 A1 | 12/2009 | Van Vorhis et al. |
| 2010/0152782 A1* | 6/2010 | Stone ................. A61B 17/152 606/280 |
| 2010/0153076 A1 | 6/2010 | Bellettre et al. |
| 2011/0066079 A1 | 3/2011 | Otto et al. |
| 2011/0082462 A1 | 4/2011 | Suarez et al. |
| 2012/0016427 A1* | 1/2012 | Stindel et al. ............. 606/86 R |
| 2013/0169423 A1 | 7/2013 | Iorgulescu et al. |
| 2013/0172905 A1 | 7/2013 | Iorgulescu et al. |
| 2013/0173008 A1 | 7/2013 | Bechtold et al. |

FOREIGN PATENT DOCUMENTS

| | | |
|---|---|---|
| CN | 101484086 A | 7/2009 |
| WO | WO-02/37935 | 5/2002 |

* cited by examiner

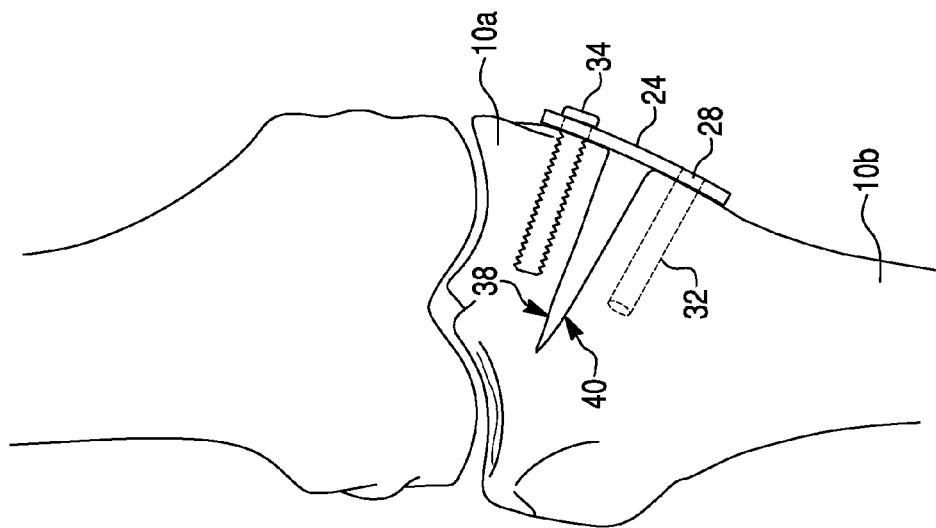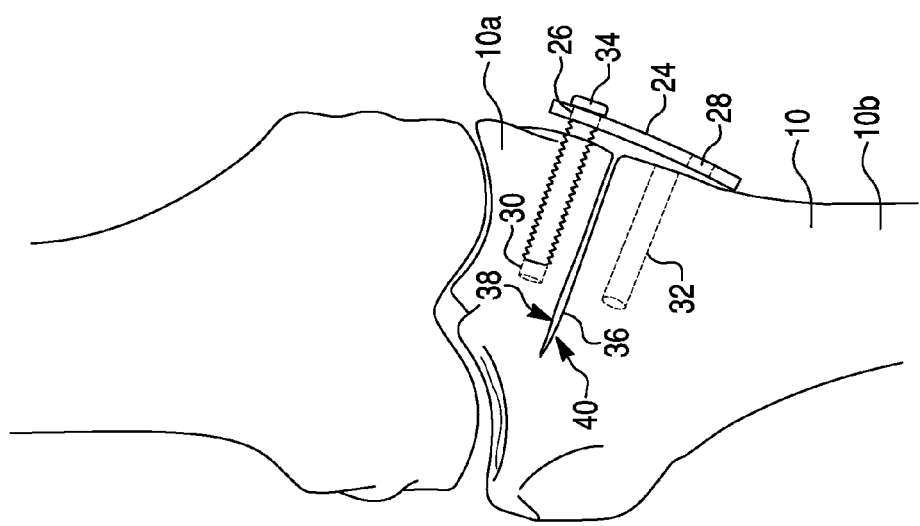

METHODS AND SYSTEMS FOR PLANNING AND PERFORMING AN OSTEOTOMY

BACKGROUND

This application relates to osteotomy procedures and, more particularly, to methods and systems for planning and performing osteotomy procedures.

An osteotomy is a surgical procedure in which a bone is cut and reconfigured, often to correct a misaligned joint. Misaligned joints can cause osteoarthritis, or degradation of articular cartilage, resulting in pain, stiffness, and swelling. By realigning the joint, an osteotomy procedure relieves pressure on a portion of the joint by shifting the load-bearing axis.

Osteotomy procedures to reconfigure the tibia or femur can relieve pain and other symptoms resulting from osteoarthritis of the knee. In an open wedge osteotomy, a cut is made through a portion of the bone and the opposing surfaces of the cut are pulled apart to create a wedge-shaped opening, which can then be filled by bone graft. In a closing wedge osteotomy, a wedge-shaped portion of bone is removed, and the opposing surfaces are brought together to close the opening.

Conventional osteotomies are technically challenging procedures to plan and perform. One current planning method includes drawing a planned cut or wedge to be removed onto a two-dimensional image of the joint. There are numerous challenges associated with accurately planning a surgical procedure using a two-dimensional image when the surgery is executed on a three-dimensional portion of the anatomy. One difficulty associated with conventional planning techniques includes the lack of tools to analyze the surgical plan in terms of the structural soundness (i.e. integrity) of the planned post-operative bone. Without analyzing the predicted structural soundness of the bone, osteotomies performed according to plan may result in post-operative fractures of the tibia.

In addition to the challenges of planning osteotomy procedures, surgeons also face challenges during implementation. During high tibial osteotomies, for example, the surgeon attempts to achieve a specific desired angle between the femur and tibia (e.g. the femoral-tibial alignment angle). Studies have shown that a femoral-tibial angle of 7-13 degrees of valgus alignment results in beneficial long-term clinical outcomes. High tibial osteotomies attempt to achieve the desired femoral-tibial angle by adding bone to the tibia (open wedge osteotomy) or by removing bone from the tibia (closing wedge osteotomy). In both open and closing wedge osteotomies, it is necessary to calculate the "wedge correction angle" based on the desired femoral-tibial angle. In an open wedge osteotomy, the wedge correction angle refers to the desired final angle between the resected surfaces. In a closing wedge osteotomy, the "wedge correction angle" refers to the initial angle between resected surfaces of the bone after removal of the wedge, but prior to bringing the resected surfaces together.

Often, it is difficult to determine whether the desired wedge correction angle, and therefore, the desired alignment between the two bones of the joint, has been achieved by the osteotomy procedure. This difficulty arises even during image-guided surgeries in which a navigation system tracks the bones of the joint. For example, during high tibial osteotomies, a navigation system tracks a marker attached to the tibia. However, once the surgeon cuts through all or a portion of the tibia and moves the resected surfaces relative to each other, the tracking system is no longer able to determine the pose (i.e. position and orientation) of the portion of the tibia on the non-tracked side of the cut. The surgeon therefore cannot rely on a display of the tracked bones to determine, for example, how far to increase the angle between the resected surfaces in an open wedge osteotomy.

Another challenge associated with conventional osteotomy procedures is lack of control of the saw blade used for cutting the bone, particularly in the anterior-posterior plane. Lack of adequate control can cause inaccuracies in the resulting alignment of the joint.

A further challenge associated with conventional osteotomy procedures results from the use of K-wires and fluoroscopy to verify the planned cutting plane. Resections of the bone may be performed by using K-wires as cutting guides. The K-wires are pushed into the bone, and fluoroscopic images are taken of the bone and K-wires to evaluate, for example, the planned placement of the cutting plane and fixation plate screws. This portion of the planning process exposes the patient to additional radiation.

SUMMARY

One embodiment of the invention relates to a method for performing an osteotomy. The method includes providing a fixation plate defining a first aperture and a second aperture; creating a first hole and a second hole in a bone; coupling the fixation plate to the bone by aligning the first aperture of the fixation plate and the first hole of the bone and inserting a fastener through the first aperture and into the first hole; creating a cut through at least a portion of the bone to create a first resected surface and a second resected surface after creating the first hole and the second hole; moving the first resected surface and the second resected surface relative to each other until the second aperture of the fixation plate is aligned with the second hole of the bone; and coupling the fixation plate to the bone by inserting a second fastener through the second aperture of the fixation plate and into the second hole of the bone.

An additional embodiment relates to a surgical system including a fixation plate defining a first aperture and a second aperture. The surgical system further includes a processing circuit configured to calculate a correction angle; develop a surgical plan based at least in part on the correction angle; and facilitate implementation of the surgical plan, wherein the cut is created after the first hole and the second hole. The surgical plan includes a plurality of planned virtual boundaries representing a first hole in a bone, a second hole in the bone, and a cut through at least a portion of the bone. The first and second apertures of the fixation plate are configured to align with the first and second holes in the bone after implementation of the surgical plan.

A still further embodiment relates to a computer-readable storage medium having instructions thereon that, when executed by a processing circuit, aid in the planning or performance of an open wedge osteotomy. The medium includes instructions for calculating a correction angle; instructions for developing a surgical plan based at least in part on the correction angle and a parameter of a fixation plate; and instructions for facilitating implementation of the surgical plan, wherein the cut is created after the first hole and the second hole. The surgical plan includes a plurality of planned virtual boundaries representing a first hole in a bone, a second hole in the bone, and a cut through at least a portion of the bone.

Alternative exemplary embodiments relate to other features and combinations of features as may be generally recited in the claims.

BRIEF DESCRIPTION OF THE FIGURES

The disclosure will become more fully understood from the following detailed description, taken in conjunction with the accompanying figures, wherein like reference numerals refer to like elements, in which:

FIG. 5A is an illustration of an open wedge osteotomy procedure prior to distraction of the bone according to an exemplary embodiment.

FIG. 5B is an illustration of an open wedge osteotomy procedure after distraction of the bone according to an exemplary embodiment.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

One type of osteotomy procedure is a high tibial osteotomy. In a high tibial osteotomy, the tibia can be reconfigured to shift the weight distribution on the cartilage of the knee. Two different procedures for performing high tibial osteotomies include open wedge and closing wedge.

Figure 1A:
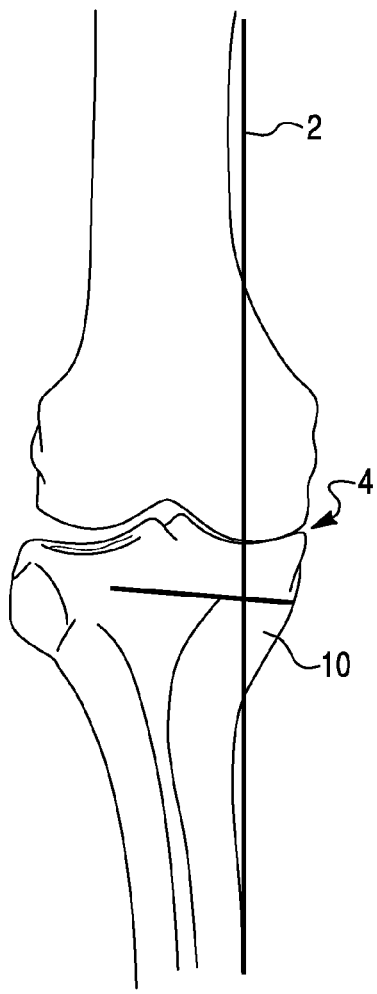
FIGS. 1A and 1B are illustrations of the load-bearing axis of a leg before and after an osteotomy procedure.
Figure 1B:
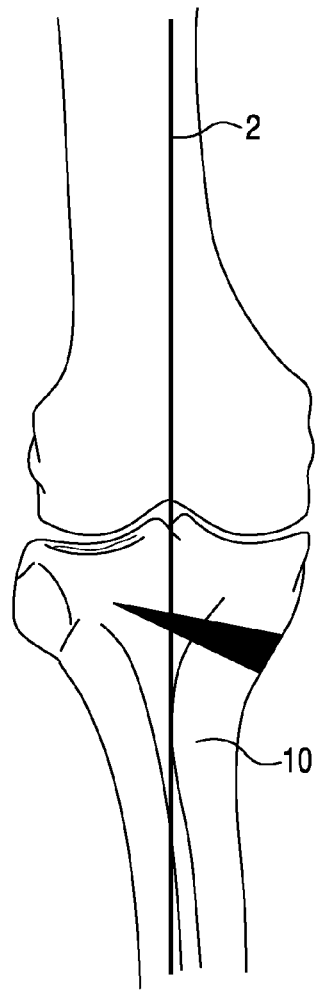

FIGS. 1A and 1B illustrate an open wedge osteotomy procedure and a corresponding shift in the load-bearing axis 2 of the leg. In FIG. 1A, the load-bearing axis 2 travels through the medial compartment 4 of the knee. After performance of an osteotomy procedure, as shown in FIG. 1B, the load-bearing axis 2 passes through the center of the knee, relieving pressure on the cartilage of the medial compartment 4.

Figure 2A:
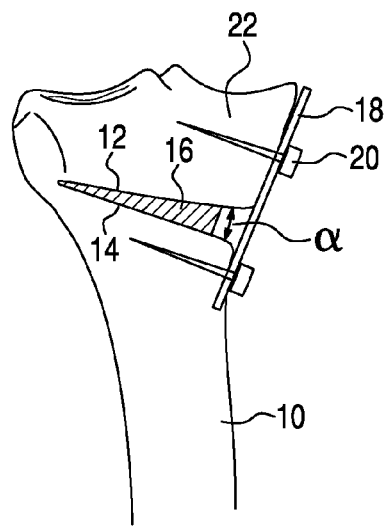
FIG. 2A is an illustration of a completed open wedge osteotomy procedure performed on a tibia.

FIG. 2A illustrates a completed high tibial, open wedge osteotomy. In an open wedge osteotomy, a surgeon cuts through all or part of a bone 10. In the embodiment of FIG. 2A, bone 10 is a tibia. The angle between the resected surfaces 12, 14 is then increased to a desired angle α, and the resulting wedge is filled with bone graft material 16. As used herein with respect to surgical methods and systems, the term "desired" means a planned or ideal outcome to be achieved by the surgical method or system.

Figure 2B:
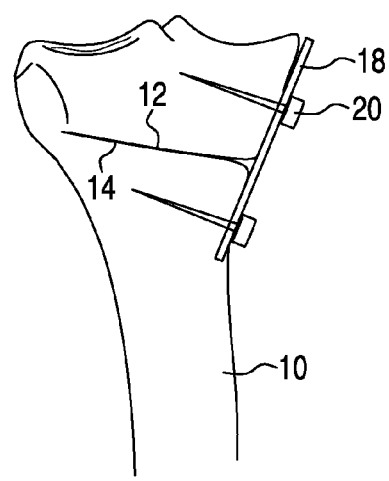
FIG. 2B is an illustration of a completed closing wedge osteotomy procedure performed on a tibia.

FIG. 2B illustrates a completed high tibial, closing wedge osteotomy. During a closing wedge osteotomy, a wedge of bone is removed from the tibia. The resected surfaces 12, 14 are then brought together, closing the gap between the surfaces. In both open and closing wedge osteotomies, the correctly aligned bone is held in its new configuration by fixation hardware (e.g. plates 18 and screws 20).

Figure 3:
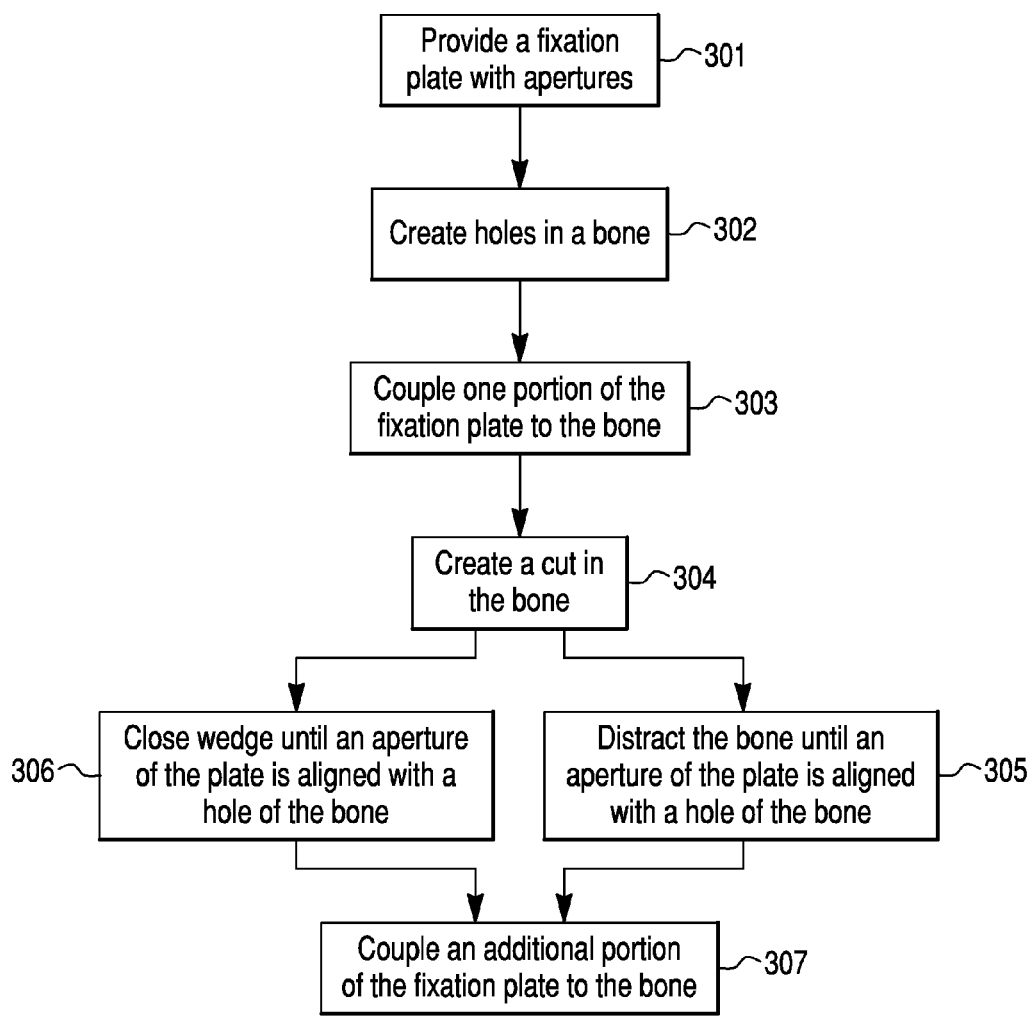
FIG. 3 is a flow chart illustrating methods for performing osteotomy procedures according to an exemplary embodiment.

FIG. 3 illustrates a method for performing an open wedge osteotomy and a method for performing a closing wedge osteotomy according to exemplary embodiments. Several embodiments described herein are discussed in relation to high tibial osteotomies. The present invention, however, is not limited to high tibial osteotomies, and the disclosed methods and systems can be utilized for osteotomy procedures on any bone of the body to correct a variety of joint alignment issues or bone abnormalities (e.g. femoral osteotomy, dentofacial osteotomy, etc.).

Figure 4:
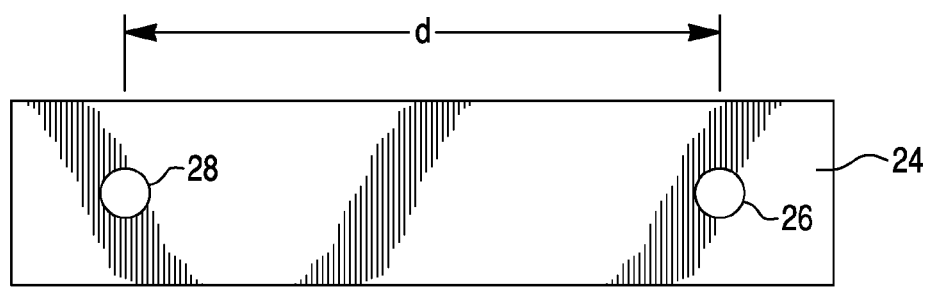
FIG. 4 is a schematic illustration of a fixation plate according to an exemplary embodiment.

In the method illustrated by FIG. 3, a fixation plate 24 is provided (step 301). The fixation plate 24 can be coupled to a bone and includes a first aperture 26 and a second aperture 28, as shown in FIG. 4. The fixation plate 24 may be generic or manufactured specifically for a patient. FIG. 4 schematically illustrates a fixation plate 24 having a set of parameters, including a distance "d" between the first aperture 26 and the second aperture 28, although the fixation plate can have any combination of parameters. A "parameter" of the plate is defined herein as any measurement, feature, or characteristic that can be used to describe the plate. Some examples of parameters include the shape of the plate; the plate's dimensions (e.g. length, width, and thickness); and the distance "d" between the first aperture 26 and the second aperture 28 of the plate. Although the fixation plate 24 is shown as rectangular in shape, the plate 24 may be any shape suitable for being coupled to a bone and maintaining the bone in a fixed position after an osteotomy procedure. The plate 24 may be oval, square, trapezoidal, or any other geometric shape. The plate 24 can also be irregularly shaped with extruding portions or cutouts. Furthermore, the dimensions of the plate 24 or portions of the plate can be uniform or non-uniform. For example, the plate 24 may vary in thickness or curvature along the length in order to conform to the contours or shape of the patient's bone. The fixation plate 24 may be made of any material suitable for implantation within a patient.

The first aperture 26 and the second aperture 28 may each receive a fastener (e.g. a screw or nail) to couple the fixation plate 24 to the patient's bone. The apertures 26, 28 can be any shape suitable for receiving a fastener (e.g. circular, oval, square, rectangular, irregular, etc.). The walls of the apertures 26, 28 may be smooth or threaded. If the walls are threaded, inserting a threaded fastener through the apertures may further stabilize the coupling between the fixation plate and the bone. The apertures 26, 28 may be designed as openings through the thickness of the fixation plate 24, through which a surgeon is able to insert a separate fastener. In an alternative embodiment, the fixation plate may be manufactured with fasteners in the apertures that are able to, for example, slide or rotate within the apertures for insertion into a patient's bone.

Holes are created in the patient's bone to accommodate the fasteners (step 302). As many holes as necessary can be created in the bone, including a first hole 30 and a second hole 32 (FIG. 5A). In FIG. 5A, first hole 30 is shown with a fastener 34 already inserted into the first hole 30. The first hole 30 and second hole 32 are located on the same bone 10. For example, if an open or closing wedge osteotomy is to be performed on bone 10, both the first hole 30 and the second hole 32 will be created on the bone 10 in accordance with a preoperative plan. In one embodiment, the first hole 30 is located in a proximal portion 10a of bone 10 and the second hole 32 is located in a distal portion 10b of bone 10 (FIG. 5A). The holes 30, 32 can be created by drilling or by any other known method of creating a hole in a bone (e.g. inserting and removing a nail or other sharp object).

Referring to FIG. 5A, the fixation plate 24 is coupled to the bone by aligning the first aperture 26 of the fixation plate and the first hole 30 of the bone 10 and inserting a fastener 34 through the first aperture 26 and into the first hole 30 (step 303). FIG. 5A illustrates one portion of the fixation plate 24 coupled to the patient's bone 10. A fastener 34 is inserted through the first aperture and into the first hole to couple the fixation plate to the bone. The fastener 34 may be any type of structure suitable for coupling the fixation plate to the bone (e.g. a bone screw or nail). In an alternative embodiment, step 303 includes aligning aperture 28 with hole 32 and coupling the fixation plate to the bone 10 by inserting a fastener through aperture 28 and into hole 32.

In one embodiment, coupling the fixation plate to the bone does not include secure and/or permanent fixation. Rather, the fastener may loosely couple the fixation plate and bone so that the uncoupled end of the plate can be rotated or adjusted during the osteotomy procedure. In an alternative embodiment, coupling the fixation plate to the bone includes secure fixation such that the plate is not easily movable relative to the portion of the bone to which the plate is coupled.

Further referring to FIG. 3, a cut (i.e. resection) is made through at least a portion of the bone (step 304). In the case of an open wedge osteotomy, the cut can be a single planar cut. Alternatively, in an open wedge osteotomy, two or more cuts can be made to remove a wedge-shaped portion of the bone, although the resulting wedge-shaped opening will subsequently be distracted. In the case of a closing wedge osteotomy, two or more cuts are made to remove a wedge-shaped portion of the bone, creating a wedge-shaped opening that will subsequently be closed. FIG. 5A illustrates a single cut 36 through the bone 10. The cut 36 may run through a portion of the bone, as illustrated in FIG. 5A, or may run all the way through the bone. The cut 36 creates a first resected surface 38 and a second resected surface 40 on opposing sides of the cut 36. After distraction of the bone during an open wedge osteotomy, as shown in FIG. 5B, the first resected surface 38 and the second resected surface 40 each face a wedge-shaped opening created between the proximal portion 10a and the distal portion 10b of the bone 10.

In one embodiment, the holes 30, 32 and the cut 36 can be created by using mechanical guides, cutting jigs, and/or templates. Additionally or alternatively, the surgeon can use a tracked cutting tool and an image-guided surgery system that provides visual and/or audible guidance during cutting.

In another embodiment, drilling of the holes 30, 32 and creation of the cut 36 can be accomplished with the assistance of a haptically guided interactive robotic system, such as the haptic guidance system described in U.S. Pat. No. 8,010,180, titled "Haptic Guidance System and Method," granted Aug. 30, 2011, and hereby incorporated by reference herein in its entirety. As the surgeon manipulates a robotic arm to drill holes in the bone or perform cuts with a high speed drill, sagittal saw, or other suitable tool, the system provides haptic feedback to guide the surgeon in sculpting the holes and cuts into the appropriate shape, which is pre-programmed into the control system of the robotic arm. Haptic guidance and feedback will be explained more fully below.

Referring again to FIG. 3, steps 305 and 306 illustrate different paths depending on whether the surgical procedure is an open wedge osteotomy or a closing wedge osteotomy. In an open wedge osteotomy, with one portion of the fixation plate 24 coupled to the bone, the bone is distracted such that the first resected surface 38 and the second resected surface 40 move relative to each other until the second aperture 28 of the fixation plate 24 is aligned with the second hole 32 of the bone 10 (step 305; see also FIG. 5B). The bone may be distracted by any known method. For example, the surgeon may manually pull the proximal portion 10a and distal portion 10b of the bone 10 apart using any suitable tool, periodically measuring the angle between the first and second resected surfaces 38, 40. The surgeon utilizes the second aperture 28 of the fixation plate 24 and the second hole 32 of the bone 10 to determine how far to distract the bone. As noted above, one challenge of performing an open wedge osteotomy is achieving the pre-planned wedge correction angle. Because the wedge correction angle determines the final femoral-tibial alignment angle, an accurate mechanism to ensure implementation of the planned wedge correction angle is critical to the success of an osteotomy procedure. The methods of performing an open wedge osteotomy described herein enable the surgeon to utilize the geometry (e.g. parameters) of the fixation plate and the drilled holes in the bone to ensure achievement of the planned wedge correction angle.

In another embodiment, distraction of the bone during an open wedge osteotomy may be accomplished with the aid of a surgical system having a robotic haptic device, such as the haptic device disclosed in U.S. Pat. No. 8,010,180. In an exemplary method, a user couples an appropriately shaped distraction tool to the haptic device and then interacts with the haptic device to guide the end of the tool between the first resected surface 38 and second resected surface 40. The surgical system then controls the haptic device to distract the bone until the desired correction angle (i.e. the angle between the first and second resected surfaces) is achieved. In one approach, the haptic device slowly pushes the tool between the surfaces, automatically stopping once the desired correction angle between the first and second resected surfaces has been reached.

In a closing wedge osteotomy, rather than distracting the resected surfaces, the wedge-shaped opening created in the bone is closed. In other words, the resected surfaces created by removing a wedge-shaped portion of the bone are brought together. Once the wedge has been closed, the second aperture of the fixation plate is aligned with the second hole in the bone (step 306).

Referring again to FIG. 3, once the first portion of the fixation plate has been coupled to the bone, the surgeon has achieved the desired wedge correction angle (open wedge osteotomy) or closed the wedge correction angle (closing wedge osteotomy), and the second aperture 28 of the fixation plate 24 is aligned with the second hole 32 of the bone 10, the second portion of the fixation plate 24 can be coupled to the bone 10 by inserting a second fastener through the second aperture 28 of the fixation plate 24 and into the second hole 32 of the bone 10 (step 307). Step 307 is accomplished in a similar manner as step 303, described above. In the embodiment of FIG. 5A, the first portion of fixation plate 24 is coupled to the bone 10 with fastener 34 prior to coupling the second portion of fixation plate 24 to bone 10 (e.g. by inserting a fastener through second aperture 28 and into second hole 32). However, this order may be reversed such that the second portion of the fixation plate 24 is coupled to bone 10 prior to coupling the first portion of the fixation plate 24 to bone 10. In other words, a fastener may be inserted through second aperture 28 and into second hole 32 prior to inserting fastener 34 through first aperture 26 and into first hole 30.

Figure 6:
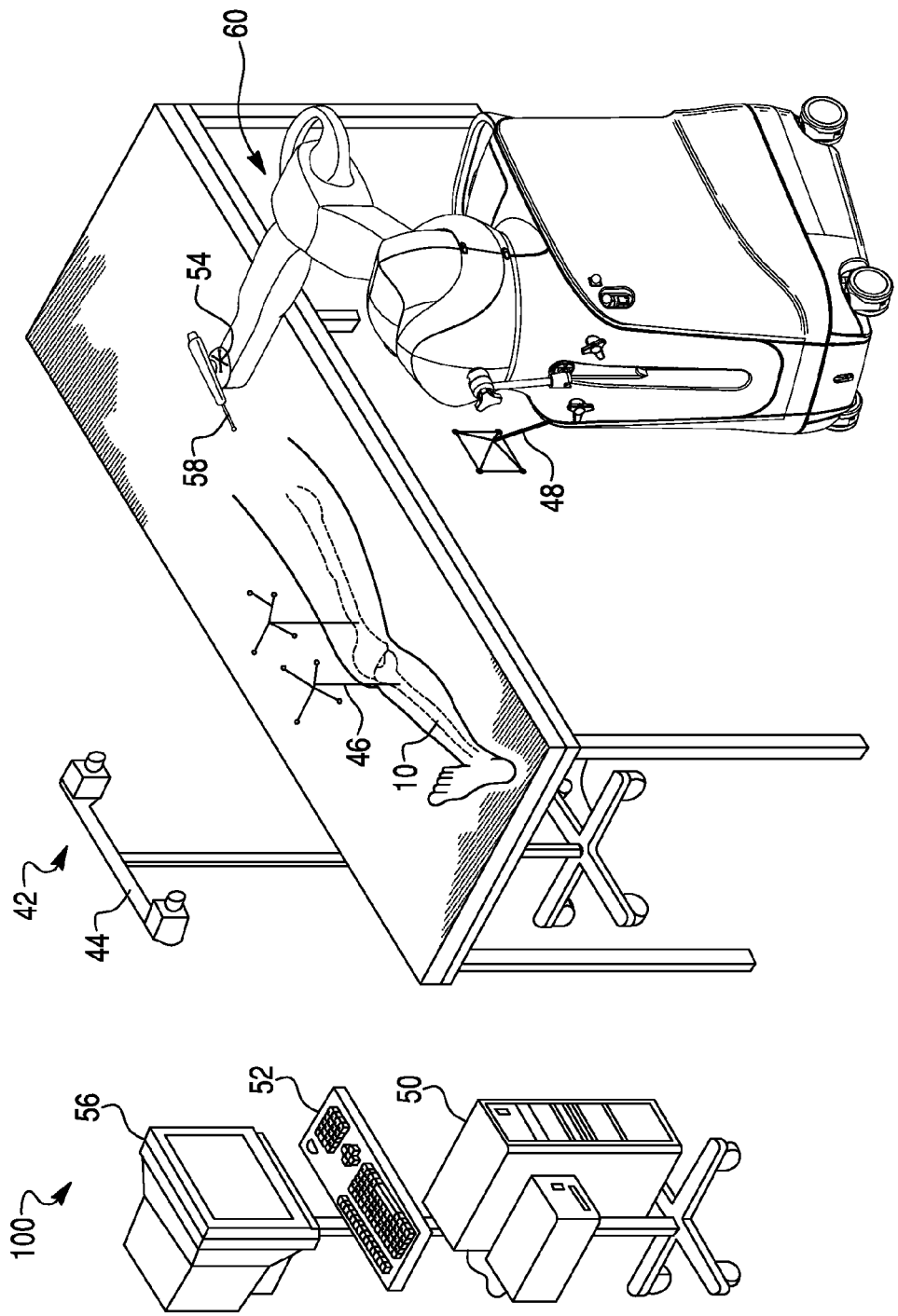
FIG. 6 is an illustration of a surgical system according to an exemplary embodiment.

Referring to FIG. 6, according to an exemplary embodiment, a surgical system 100 includes a navigation system 42, a computer 50, and a haptic device 60. The navigation system tracks the patient's bone, as well as surgical tools utilized during the surgery, to allow the surgeon to visualize the bone and tools on a display 56 during the osteotomy procedure.

The navigation system 42 may be any type of navigation system configured to track the pose (i.e. position and orientation) of a bone. For example, the navigation system 42 may include a non-mechanical tracking system, a mechanical tracking system, or any combination of non-mechanical and mechanical tracking systems. The navigation system 42 includes a detection device 44 that obtains a pose of an object with respect to a coordinate frame of reference of the detection device 44. As the object moves in the coordinate frame of reference, the detection device tracks the pose of the object to detect movement of the object.

In one embodiment, the navigation system 42 includes a non-mechanical tracking system as shown in FIG. 6. The non-mechanical tracking system is an optical tracking system with a detection device 44 and a trackable element (e.g. navigation marker 46) that is disposed on a tracked object and is detectable by the detection device 44. In one embodiment, the detection device 44 includes a visible light-based detector, such as a MicronTracker (Claron Technology Inc., Toronto, Canada), that detects a pattern (e.g., a checkerboard pattern) on a trackable element. In another embodiment, the detection device 44 includes a stereo camera pair sensitive to infrared radiation and positionable in an operating room where the osteotomy procedure will be performed. The trackable element is affixed to the tracked object in a secure and stable manner and includes an array of markers having a known geometric relationship to the tracked object. As is known, the trackable elements may be active (e.g., light emitting diodes or LEDs) or passive (e.g., reflective spheres, a checkerboard pattern, etc.) and have a unique geometry (e.g., a unique geometric arrangement of the markers) or, in the case of active, wired markers, a unique firing pattern. In operation, the detection device 44 detects positions of the trackable elements, and the surgical system 100 (e.g., the detection device 44 using embedded electronics) calculates a pose of the tracked object based on the trackable elements' positions, unique geometry, and known geometric relationship to the tracked object. The tracking system 42 includes a trackable element for each object the user desires to track, such as the navigation marker 46 located on the bone 10. During haptically guided robotic-assisted surgeries, the navigation system may further include a haptic device marker 48 (to track a global or gross position of the haptic device 60), and an end effector marker 54 (to track a distal end of the haptic device 60).

After creation of a cut 36 in bone 10 during an osteotomy procedure, navigation marker 46 will be located on one side of cut 36. Subsequent movement of portions of bone 10 together (e.g., during a closing wedge osteotomy) or apart (e.g., during an open wedge osteotomy) may cause the navigation system 42 to be unable to track the portion of bone 10 located on the opposite side of cut 36 from navigation marker 46. For example, referring to FIGS. 5A and 5B, either proximal portion 10a or distal portion 10b may no longer be accurately tracked after creation of cut 36 and subsequent movement of portions 10a and 10b relative to each other. An inability of the navigation system 42 to track a portion of bone 10 during the osteotomy procedure can cause loss of registration (described further below) between the non-tracked portion of the bone and the preoperative three-dimensional representation of the bone 10. Loss of registration can impede the ability to use a haptic device 60 to create holes 30, 32 and cut 36. One beneficial option to overcome certain disadvantages associated with an inability to track a portion of bone 10 after creation of cut 36 is to drill first hole 30 and second hole 32 prior to creation of cut 36. Both portions 10a and 10b of bone 10 will therefore be tracked during creation of first hole 30, second hole 32, and cut 36. Another option to overcome an inability to track both portions 10a and 10b during an osteotomy procedure is to have a navigation marker on each side of the planned location of cut 36.

Referring again to FIG. 6, the surgical system 100 further includes a processing circuit, represented in the figures as a computer 50. The processing circuit includes a processor and memory device. The processor can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes, layers and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit and includes computer code for executing (e.g., by the processing circuit and/or processor) one or more processes described herein.

The computer 50 is configured to communicate with the navigation system 42 and the haptic device 60. Furthermore, the computer 50 may receive information related to osteotomy procedures and perform various functions related to performance of osteotomy procedures. For example, the computer 50 may have software as necessary to perform functions related to image analysis, surgical planning, registration, navigation, image guidance, and haptic guidance.

Figure 8:
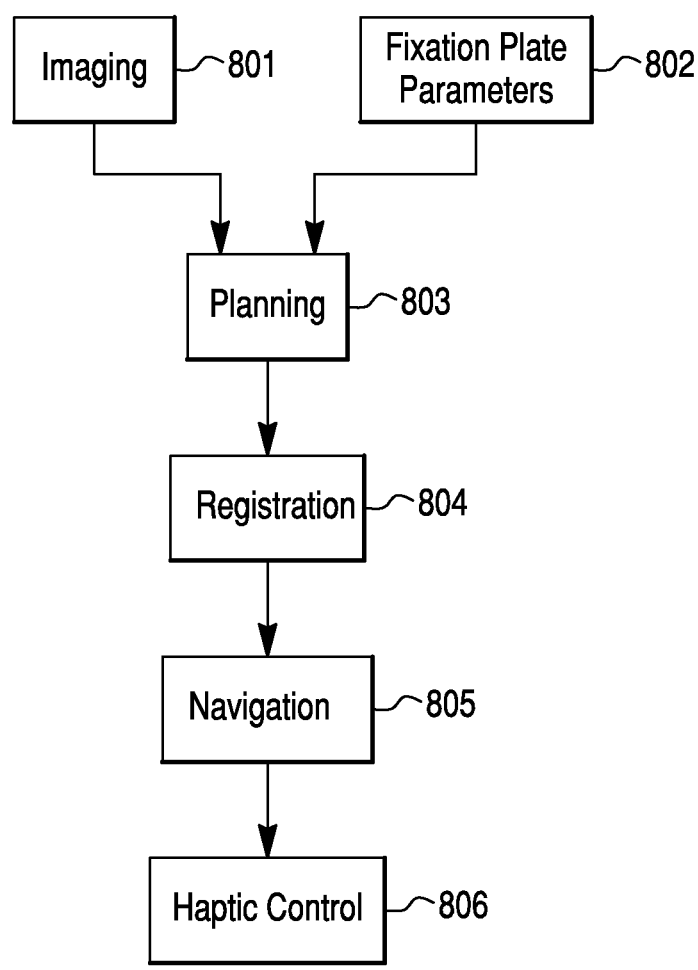
FIG. 8 is a flow chart illustrating surgical planning and performance of an osteotomy according to an exemplary embodiment.

The computer 50 receives images of the patient's anatomy on which an osteotomy procedure is to be performed. Referring to FIG. 8, prior to performance of an osteotomy, the patient's anatomy is scanned using any known imaging technique, such as CT or MRI (step 801). The scan data is then segmented to obtain a three-dimensional representation of the patient's anatomy. For example, prior to performance of a high tibial osteotomy, a three-dimensional representation of the femur and tibia is created. Using the three-dimensional representation and as part of the planning process, femoral and tibial landmarks can be selected, and the patient's femoral-tibial alignment angle is calculated. The femoral and tibial landmarks may include the femoral head center, the tibia-ankle center, and the medial tibial spine. The femoral-tibial alignment angle is the angle between a line connecting the femoral head center and the medial tibial spine and a line connecting the medial tibial spine to the tibia-ankle center. Based on the patient's current femoral-tibial angle and the desired femoral-tibial alignment angle to be achieved by the osteotomy procedure, the computer 50 is programmed to calculate the desired correction angle.

The correction angle can represent any angular measurement utilized for planning holes to be drilled in a bone and/or a cut to be made through at least a portion of a bone during an osteotomy procedure. For example, in an open wedge osteotomy procedure, the correction angle can be the desired angle between first and second resected surfaces created by a cut through the bone, also referred to as the wedge correction angle. In an open wedge osteotomy, the wedge correction angle is ideally achieved after the two resected surfaces have been distracted and the osteotomy procedure is complete. In a closing wedge osteotomy procedure, the correction angle can be the angle between two resected surfaces on either side of a wedge to be removed from the bone. Alternatively, in either an open or closing wedge osteotomy procedure, the correction angle can refer to or be a function of the angle between two bones of a joint. For example, the correction angle can be any one of: (a) a desired angle between a femur and a tibia; (b) a difference between (i) a current angle between the femur and the tibia and (ii) the desired angle between the femur and the tibia; and (c) a function of the desired angle between the femur and the tibia.

Figure 7B:
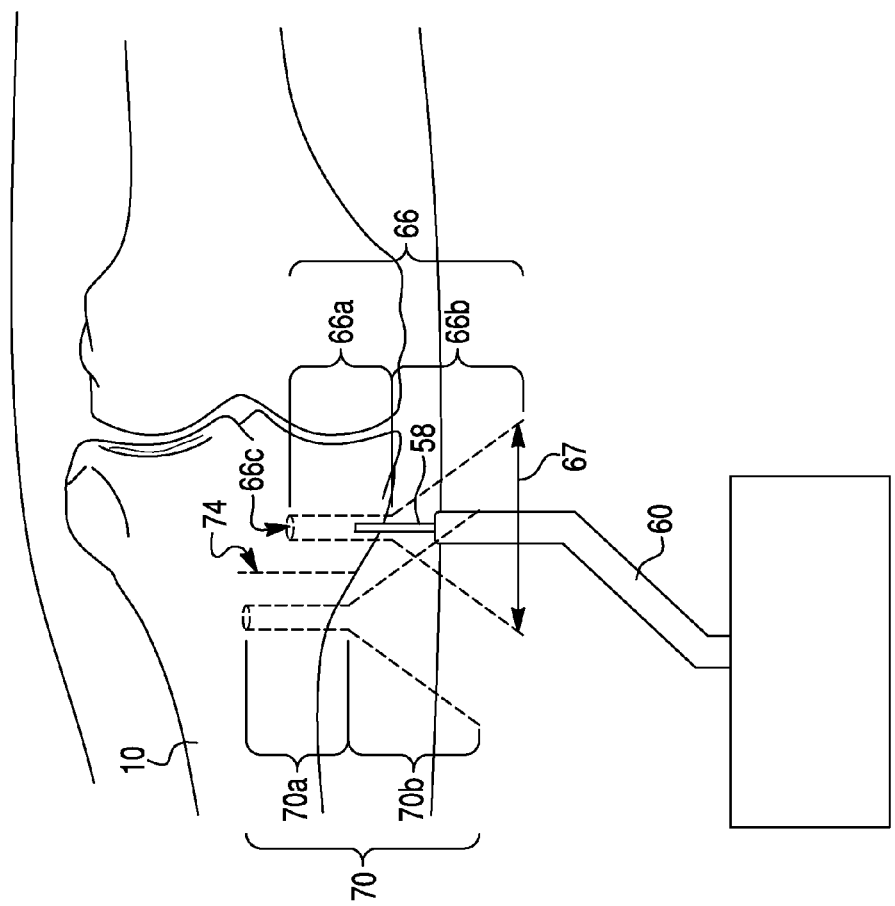
FIGS. 7A and 7B illustrate haptic guidance during performance of an osteotomy according to an exemplary embodiment.
Figure 7A:
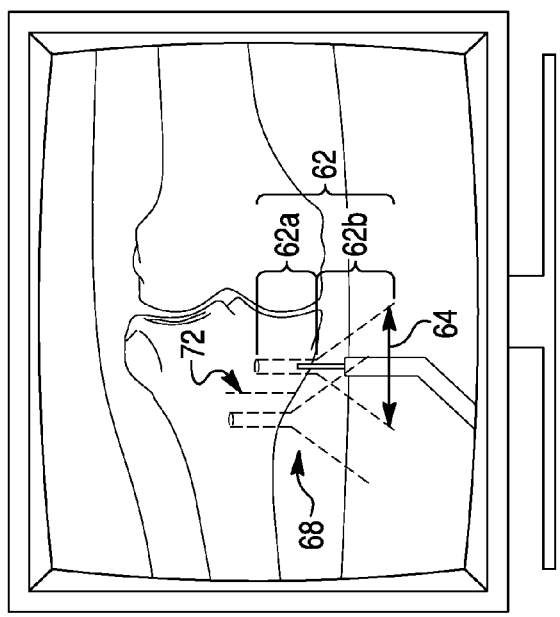

After the correction angle has been calculated by the computer 50, the computer 50 is used to develop a surgical plan based at least in part on the correction angle (step 803). It should be understood that a user can interact with the computer 50 at any stage during surgical planning to input information and modify any portion of the surgical plan. The surgical plan includes a plurality of planned virtual boundaries. The virtual boundaries, shown in FIG. 7A, represent holes and/or cuts to be made in a bone 10 during an osteotomy procedure. Specifically, the virtual boundaries can represent a first hole 30 in a bone 10, a second hole 32 in the bone 10, and a cut 36 through at least a portion of the bone 10. Once the surgical plan has been developed, a haptic device 60 is used to assist a user in creating the planned holes 30, 32 and cut 36.

During surgical planning, the computer 50 further receives information related to a fixation plate 24 to be used during the osteotomy procedure (e.g. the "selected fixation plate") (step 802). For example, a user may input parameters of a selected fixation plate 24 into the computer 50 using the input device 52 (e.g. keyboard, mouse, etc.). Alternatively, the computer 50 may contain a pre-established database of various fixation plates and their parameters, and a user can choose the selected fixation plate 24 from the database. In a still further embodiment, the fixation plate 24 may be custom designed based on a patient-specific surgical plan. Selection of the fixation plate 24 may occur during any stage of surgical planning.

The surgical plan may further be based on at least one parameter of the fixation plate 24 or a function of a parameter of the fixation plate 24. Because the fixation plate 24 can be selected at any stage of the surgical planning process, the fixation plate 24 may be selected prior to or after determination of the planned virtual boundaries by the computer 50. If the fixation plate 24 is selected first, the planned virtual boundaries may be based at least in part on a parameter of the fixation plate 24. For example, the distance (or any other relationship) between the planned virtual boundaries representing the first and second holes 30, 32 in the bone 10 may be planned based on the desired correction angle and the distance between the first and second apertures 26, 28 of the fixation plate 24 (or any other parameter of the fixation plate). In this manner, implementation of the surgical plan (e.g. creation of the holes 30, 32, creation of a cut 36, distraction of the resected surfaces, etc.) will result in alignment of the first and second holes 30, 32 in the bone 10 with the first and second apertures 26, 28 of the fixation plate 24. Alternatively, the computer 50 may develop the surgical plan, including the planned virtual boundaries, prior to fixation plate selection. In this case, the fixation plate 24 may be selected (e.g. input, chosen, or designed) based at least in part on the planned virtual boundaries. For example, the fixation plate 24 can be selected based on the planned virtual boundaries such that execution of the surgical plan will result in alignment of the first and second holes 30, 32 in the bone 10 with the first and second apertures 26, 28 of the fixation plate 24.

The virtual boundaries exist in virtual space and can be representative of features existing or to be created in physical (i.e. real) space. Virtual boundaries correspond to working boundaries in physical space that are capable of interacting with objects in physical space. For example, working boundaries can interact with a surgical tool 58 coupled to haptic device 60. Although the surgical plan is often described herein to include virtual boundaries representing a first hole 30, a second hole 32, and a cut 36, the surgical plan may include virtual boundaries representing additional holes, cuts, or other modifications to a bone 10. Furthermore, virtual boundaries may correspond to any working boundary in physical space capable of interacting with objects in physical space.

Referring to FIG. 8, after surgical planning and prior to performing an osteotomy, the physical anatomy (e.g. bone 10) is registered to a virtual representation of the anatomy (e.g. a preoperative three-dimensional representation) using any known registration technique (step 804). Possible registration techniques include the point-based registration technique described in above-referenced U.S. Pat. No. 8,010,180, or 2D/3D registration utilizing a hand-held radiographic imaging device as described in U.S. application Ser. No. 13/562,163, titled "Radiographic Imaging Device," filed Jul. 30, 2012, and hereby incorporated by reference herein in its entirety. Registration of the patient's anatomy allows for accurate navigation during the surgical procedure (step 805), which enables each of the virtual boundaries to correspond to a working boundary in physical space. For example, referring to FIGS. 7A and 7B, a virtual boundary 62 representing a first hole in a bone 10 corresponds to a working boundary 66 in physical space. A portion of working boundary 66 in turn corresponds to the planned location of the first hole 30 in the bone 10.

The virtual boundaries and, therefore, the corresponding working boundaries, can be any configuration or shape. Referring to FIG. 7A, virtual boundaries 62 and 68, representing the first and second holes 30, 32 to be created in a bone 10, may be any configuration suitable for assisting a user during creation of the first and second holes 30, 32. Portions of virtual boundaries 62 and 68, illustrated within the virtual representation of the bone 10, represent bone to be removed by a surgical tool. Similarly, virtual boundary 72, representing a cut 36 through at least a portion of the bone, may be any configuration suitable for assisting a user during creation of the cut 36. The virtual boundaries (and therefore, the corresponding working boundaries) may include a surface or surfaces that fully enclose and surround a three-dimensional volume. In an alternative embodiment, the virtual and working boundaries do not fully enclose a three-dimensional volume, but rather include both "active" surfaces and "open" portions. For example, virtual boundary 62 representing a first hole in a bone may have an essentially cylindrical "active" surface and a funnel-shaped "active" surface connected to the cylindrical portion, with an "open" portion 64. In one embodiment, virtual boundaries 62, 68 can be created with a collapsing funnel as described in U.S. application Ser. No. 13/340,668, titled "Systems and Methods for Selectively Activating Haptic Guide Zones," filed Dec. 29, 2011, and hereby incorporated by reference herein in its entirety. The working boundary 66 corresponding to virtual boundary 62 has the same configuration as virtual boundary 62. In an additional embodiment, the virtual boundary 62 representing the first hole 30 in the bone 10 includes only the substantially cylindrical portion 62a. An end of a virtual boundary having only a cylindrical portion may have an "open" top such that the open top of the corresponding working boundary coincides with the outer surface of the bone 10. Alternatively, as shown in FIGS. 7A and 7B, the cylindrical working boundary portion 66a corresponding to virtual boundary portion 62a may extend past the outer surface of the bone 10. The virtual boundary 68 representing a second hole 32 in the bone 10 may have the same configuration as virtual boundary 62 or may have a different configuration, depending on the surgical plan. Working boundary 70 corresponding to virtual boundary 68 has the same configuration as virtual boundary 68.

Virtual boundary 72 representing a cut through a portion of the bone may have an essentially planar shape. Alternatively, virtual boundary 72 can be curved or have an irregular shape. Virtual boundary 72 may also have a thickness, although FIG. 7A schematically illustrates virtual boundary 72 as a line. For example, virtual boundary 72 may be slightly thicker than a surgical tool used to create the cut in the bone, such that the tool can be constrained within the active surfaces of working boundary 74 while within the bone. Virtual boundary 72 may be planned such that the corresponding working boundary 74 extends past the outer surface of the bone 10 in a funnel or other appropriate shape to assist a surgeon as the surgical tool 58 is approaching the bone 10. Haptic guidance and feedback (as described below) can be provided to a user based on relationships between surgical tool 58 and the active surfaces of working boundaries.

The surgical plan may also include virtual boundaries to facilitate entry into and exit from haptic control, including automatic alignment of the surgical tool, as described in U.S. application Ser. No. 13/725,348, titled "Systems and Methods for Haptic Control of a Surgical Tool," filed Dec. 21, 2012, and hereby incorporated by reference herein in its entirety.

The surgical plan, including the virtual boundaries, may be developed based on information related to the patient's bone density. The density of a patient's bone is calculated using data obtained from the CT, MRI, or other imaging of the patient's anatomy. In one embodiment, a calibration object representative of human bone and having a known calcium content is imaged to obtain a correspondence between image intensity values and bone density measurements. This correspondence can then be applied to convert intensity values of individual images of the patient's anatomy into bone density measurements. The individual images of the patient's anatomy, with the corresponding map of bone density measurements, are then segmented and used to create a three-dimensional representation (i.e. model) of the patient's anatomy, including the patient's bone density information. Image analysis, such as finite element analysis (FEA), may then be performed on the model to evaluate its structural integrity.

The ability to evaluate the structural integrity of the patient's anatomy improves the effectiveness of osteotomy planning. For example, if certain portions of the patient's bone appear less dense (i.e. osteoporotic), the holes and cuts can be planned to minimize the risk of fracture of the weakened portions of bone. Furthermore, the planned structure of the bone after implementation of the surgical plan (e.g. the post-operative bone) can also be evaluated for structural integrity, pre-operatively, to improve surgical planning. In this embodiment, holes and/or cuts are planned and the model is manipulated to represent the patient's bone after performance of the osteotomy procedure. For example, a model may be created of the patient's bone after performance of an open wedge osteotomy, during which the resected surfaces have been distracted, a bone graft has been added, and the fixation plate has been coupled to the bone. The patient's bone may also be modeled after a closing wedge osteotomy, during which the wedge-shaped opening has been closed and a fixation plate has been coupled to the bone. Various other factors affecting the structural integrity of the post-operative bone may be taken into account, such as the patient's weight and lifestyle. The structural integrity of the post-operative bone is analyzed to determine whether the patient's bone will be structurally sound post-operatively. If the analysis uncovers structural weaknesses, the surgical plan can be modified to achieve a desired post-operative structural integrity.

Once the surgical plan has been finalized, a surgeon may perform the osteotomy procedure with the assistance of haptic device 60 (step 806). Through haptic device 60, the surgical system 100 provides haptic guidance and feedback to the surgeon to help the surgeon accurately implement the surgical plan. Haptic guidance and feedback during an osteotomy procedure allows for greater control of the surgical tool compared to conventional osteotomy techniques, resulting in more accurate alignment correction. Furthermore, haptic guidance and feedback is intended to eliminate the need to use K-wires and fluoroscopy for planning purposes. Instead, the surgical plan is created and verified using the three-dimensional representation of the patient's anatomy, and the haptic device provides guidance during the surgical procedure.

"Haptic" refers to a sense of touch, and the field of haptics relates to human interactive devices that provide tactile and/or force feedback to an operator. Tactile feedback generally includes tactile sensations such as, for example, vibration. Force feedback (also known as "wrench") refers to feedback in the form of force (e.g., resistance to movement) and/or torque. Wrench includes, for example, feedback in the form of force, torque, or a combination of force and torque. Haptic feedback may also encompass disabling or altering the amount of power provided to the surgical tool, which can provide tactile and/or force feedback to the user.

Surgical system 100 provides haptic feedback to the surgeon based on a relationship between surgical tool 58 and at least one of the working boundaries. The relationship between surgical tool 58 and a working boundary can be any suitable relationship between surgical tool 58 and a working boundary that can be obtained by the navigation system and utilized by the surgical system 100 to provide haptic feedback. For example, the relationship may be the position, orientation, pose, velocity, or acceleration of the surgical tool 58 relative to one or more working boundaries. The relationship may further be any combination of position, orientation, pose, velocity, and acceleration of the surgical tool 58 relative to one or more working boundaries. The "relationship" between the surgical tool 58 and a working boundary may also refer to a quantity or measurement resulting from another relationship between the surgical tool 58 and a working boundary. In other words, a "relationship" can be a function of another relationship. As a specific example, the "relationship" between the surgical tool 58 and a working boundary may be the magnitude of a haptic force generated by the positional relationship between the surgical tool 58 and a working boundary.

During operation, a surgeon manipulates the haptic device 60 to guide a surgical tool 58 coupled to the device. The surgical system 100 provides haptic feedback to the user, through haptic device 60, to assist the surgeon during creation of the planned holes, cuts, or other modifications to the patient's bone.

For example, the surgical system 100 may assist the surgeon by substantially preventing or constraining the surgical tool 58 from crossing a working boundary. The surgical system 100 may constrain the surgical tool from crossing a working boundary by any number and combination of haptic feedback mechanisms, including by providing tactile feedback, by providing force feedback, and/or by altering the amount of power provided to the surgical tool. "Constrain," as used herein, is used to describe a tendency to restrict movement. Therefore, the surgical system may constrain the surgical tool 58 directly by applying an opposing force to the haptic device 60, which tends to restrict movement of the surgical tool 58. The surgical system may also constrain the surgical tool 58 indirectly by providing tactile feedback to alert a user to change his or her actions, because alerting a user to change his or her actions tends to restrict movement of the surgical tool 58. In a still further embodiment, the surgical system 100 may constrain the surgical tool 58 by limiting power to the surgical tool 58, which again tends to restrict movement of the tool.

In various embodiments, the surgical system 100 provides haptic feedback to the user as the surgical tool 58 approaches a working boundary, upon contact of the surgical tool 58 with the working boundary, and/or after the surgical tool 58 has penetrated the working boundary by a predetermined depth. The surgeon may experience the haptic feedback, for example, as a vibration, as a wrench resisting or actively opposing further movement of the haptic device, or as a solid "wall" substantially preventing further movement of the haptic device. The user may alternatively experience the haptic feedback as a tactile sensation (e.g. change in vibration) resulting from alteration of power provided to the surgical tool 58, or a tactile sensation resulting from cessation of power provided to the tool. If power to the surgical tool is altered or stopped when the surgical tool 58 is drilling, cutting, or otherwise operating directly on bone, the surgeon will feel haptic feedback in the form of resistance to further movement because the tool is no longer able to drill, cut, or otherwise move through the bone. In one embodiment, power to the surgical tool is altered (e.g. power to the tool is decreased) or stopped (e.g. the tool is disabled) upon contact between the surgical tool 58 and a working boundary. Alternatively, the power provided to the surgical tool 58 may be altered (e.g. decreased) as the surgical tool 58 approaches a working boundary.

In another embodiment, the surgical system 100 may assist the surgeon in creating the planned holes, cuts, and other modifications to the bone by providing haptic feedback to guide the surgical tool 58 towards or along a working boundary. As one example, the surgical system 100 may provide forces to the haptic device 60 based on a positional relationship between the tip of surgical tool 58 and the closest coordinates of a working boundary. These forces may cause the surgical tool 58 to approach the closest working boundary. Once the surgical tool 58 is substantially near to or contacting the working boundary, the surgical system 100 may apply forces that tend to guide the surgical tool 58 to move along a portion of the working boundary. In another embodiment, the forces tend to guide the surgical tool 58 to move from one portion of the working boundary to another portion of a working boundary (e.g. from a funnel-shaped portion of the working boundary to a cylindrical portion of a working boundary).

In yet another embodiment, the surgical system 100 is configured to assist the surgeon in creating the planned holes, cuts, and modifications to the bone by providing haptic feedback to guide the surgical tool from one working boundary to another working boundary. For example, the surgeon may experience forces tending to draw the surgical tool 58 towards working boundary 66 when the user guides the surgical tool 58 towards working boundary 66. When the user subsequently removes the surgical tool 58 from the space surrounded by working boundary 66 and manipulates the haptic device 60 such that the surgical tool 58 approaches working boundary 70, the surgeon may experience forces pushing away from working boundary 66 and towards working boundary 70.

Haptic feedback as described herein may operate in conjunction with modifications to the working boundaries by the surgical system 100. Although discussed herein as modifications to "working boundaries," it should be understood that the surgical system 100 modifies the virtual boundaries, which correspond to the working boundaries. Some examples of modifications to a working boundary include: 1) reconfiguration of the working boundary (e.g. a change in shape or size), and 2) activating and deactivating the entire working boundary or portions of the working boundary (e.g. converting "open" portions to "active" surfaces and converting "active" surfaces to "open" portions). Modifications to working boundaries, similarly to haptic feedback, may be performed by the surgical system 100 based on a relationship between the surgical tool 58 and one or more working boundaries. Modifications to the working boundaries further assist a user in creating the required holes and cuts during an osteotomy procedure by facilitating a variety of actions, such as movement of the surgical tool 58 towards a bone and cutting of the bone by the surgical tool 58.

In one embodiment, modifications to the working boundary facilitate movement of the surgical tool 58 towards a bone 10. During a surgical procedure, because the patient's anatomy is tracked by the navigation system, the surgical system 100 moves the entirety of working boundary 66 in correspondence with movement of the patient's anatomy. In addition to this baseline movement, portions of working boundary 66 may be reshaped and/or reconfigured to facilitate movement of the surgical tool 58 towards the bone 10. As one example, the surgical system may tilt funnel-shaped portion 66b of working boundary 66 relative to the cylindrical portion 66a during the surgical procedure based on a relationship between the surgical tool 58 and the working boundary 66. The working boundary 66 can therefore be dynamically modified during the surgical procedure such that the surgical tool 58 remains within the space surrounded by the portion 66b of working boundary 66 as the surgical tool 58 approaches the bone 10.

In another embodiment, working boundaries or portions of working boundaries are activated and deactivated. Activating and deactivating entire working boundaries may assist a user when the surgical tool 58 is approaching the bone 10. For example, working boundary 70 may be deactivated during the time when the surgeon is approaching working boundary 66 or when the surgical tool 58 is within the space surrounded by working boundary 66. Similarly, working boundary 66 may be deactivated after the surgeon has completed creation of first hole 30 and is ready to create second hole 32. In one embodiment, working boundary 66 may be deactivated after surgical tool 58 enters the area within funnel-portion 70b but outside of funnel-portion 66b. Activating a portion of a working boundary converts a previously open portion (e.g. open top 67) to an active surface of the working boundary. In contrast, deactivating a portion of the working boundary converts a previously active surface (e.g. the end portion 66c of working boundary 66) of the working boundary to an "open" portion.

Activating and deactivating entire working boundaries or their portions may be accomplished dynamically by the surgical system 100 during the surgical procedure. In other words, the surgical system 100 may be programmed to determine, during the surgical procedure, the presence of factors and relationships that trigger activation and deactivation of virtual boundaries or portions of the virtual boundaries. In another embodiment, a user can interact with the surgical system 100 (e.g. by using the input device 52) to denote the start or completion of various stages of the osteotomy procedure, thereby triggering working boundaries or their portions to activate or deactivate.

Although some of the examples provided above are described and illustrated in terms of open wedge osteotomies, the methods and systems provided herein may also apply to closing wedge osteotomies. For example, the virtual boundaries and corresponding working boundaries illustrated in FIGS. 7A and 7B may be altered according to a surgical plan for a closing wedge osteotomy. One change, for example, might include replacing substantially planar-shaped virtual boundary 72 with a wedge-shaped virtual boundary representing a wedge of bone to be removed by a surgical tool.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage, other magnetic storage devices, solid state storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish any connection steps, processing steps, comparison steps, and decision steps.

What is claimed is:

1. A method for performing an open or closed wedge osteotomy using a force feedback device, comprising:
   obtaining, by a processing circuit associated with a computer, a three-dimensional representation of a tibia and a femur of a knee joint of a patient;
   determining, by the processing circuit associated with the computer, using the three-dimensional representation a current alignment angle of the knee joint, wherein the current alignment angle is a current angle between a line connecting a femoral head center of the femur and a medial tibial spine of the tibia and a line connecting the medial tibial spine of the tibia to a tibial-ankle center of the tibia;
   wherein said lines intersect at an intersecting point at the medial tibial spine, and wherein said lines are not collinear, and wherein said current alignment angle is measured at said intersecting point between said lines;
   calculating, by the processing circuit, a correction angle for the tibia or the femur of the knee joint, by correlating the current alignment angle to a desired alignment angle, wherein the desired alignment angle is a desired angle between the line connecting the femoral head center of the femur and the medial tibial spine of the tibia and the line connecting the medial tibial spine of the tibia to the tibial-ankle center of the tibia;
   wherein said desired alignment angle is measured at said intersecting point between said lines, and wherein said desired alignment angle differ from said current alignment angle;

wherein the processing circuit comprises a computer-readable storage medium having instructions stored thereon, that when executed by the processing circuit cause the processing circuit to determine the current alignment angle and calculate the correction angle;

receiving, by the processing circuit, information comprising parameters related to a fixation plate, the fixation plate defining a first aperture and a second aperture:

determining, by the processing circuit, planned virtual boundaries in the three-dimensional representation of the tibia or femur, representing a first hole in the tibia or femur, a second hole in the tibia or femur, and a cut through at least a portion of the tibia or femur to create a first resected surface and a second resected surface, wherein the planned virtual boundaries are based at least in part on at least one of the parameters related to the fixation plate and the calculated correction angle, and wherein the planned virtual boundaries correspond with working boundaries of the tibia or femur in physical space;

tracking movement in the physical space of a cutting tool, by a navigation system associated with the computer, such that movement of the cutting tool in the physical space is correlated with movement of a virtual tool displayed by the processing circuit;

providing, by the processing circuit, force feedback to the cutting tool while the cutting tool creates the first hole and the second hole in the tibia or the femur, the force feedback is based on the relationship between the virtual tool and the planned virtual boundaries, to constrain the cutting tool from crossing the working boundaries;

coupling the fixation plate to the tibia or the femur by aligning the first aperture of the fixation plate and the first hole of the tibia or the femur and inserting a fastener through the first aperture and into the first hole;

providing, by the processing circuit, force feedback to the cutting tool while the cutting tool creates the cut through at least a portion of the tibia or the femur to create the first resected surface and the second resected surface after creation of the first hole and the second hole, the force feedback based on the relationship between the virtual tool and the planned virtual boundaries, to constrain the cutting tool from crossing the working boundaries; and moving the first resected surface and the second resected surface relative to each other until the second aperture of the fixation plate is aligned with the second hole of the bone, whereby the correction angle is formed between the first resected surface and the second resected surface; and coupling the fixation plate to the bone by inserting a second fastener through the second aperture of the fixation plate and into the second hole of the bone.

2. The method of claim 1, wherein the step of moving the first resected surface and the second resected surface relative to each other includes distracting the first and second resected surfaces away from each other.

3. The method of claim 1, further comprising: tracking a pose of the tibia and the femur in physical space, using the navigation system.

4. The method of claim 1, wherein the at least one parameter related to the fixation plate is a function of a distance between the first and second apertures.

5. The method of claim 1, wherein the force feedback device is a haptic device and wherein providing force feedback comprises providing haptic feedback to a user.

* * * * *